(12) United States Patent
Sakurai et al.

(10) Patent No.: US 8,017,742 B2
(45) Date of Patent: Sep. 13, 2011

(54) GENE CARRIER

(75) Inventors: Kazuo Sakurai, Himeji (JP); Seiji Shinkai, Fukuoka (JP); Taro Kimura, Dazaifu (JP); Kengo Tabata, Kobe (JP); Kazuya Koumoto, Kurume (JP); Oliver Gronwald, Kurume (JP)

(73) Assignees: Japan Science and Technology Agency, Saitama (JP); Mitsui Sugar Co., Ltd., Tokyo (JP)

( * ) Notice: Subject to any disclaimer, the term of this patent is extended or adjusted under 35 U.S.C. 154(b) by 805 days.

(21) Appl. No.: 10/465,402

(22) Filed: Jun. 19, 2003

(65) Prior Publication Data

US 2003/0216346 A1 Nov. 20, 2003

Related U.S. Application Data

(62) Division of application No. 09/889,117, filed on Sep. 19, 2001, now abandoned.

(30) Foreign Application Priority Data

Nov. 10, 1999 (JP) .................................. 11-319470
May 16, 2000 (JP) ............................... 2000-142897

(51) Int. Cl.
*C07H 1/00* (2006.01)
*C07H 21/44* (2006.01)
(52) U.S. Cl. ..................... 536/1.11; 536/23.1
(58) Field of Classification Search .................. None
See application file for complete search history.

(56) References Cited

U.S. PATENT DOCUMENTS

| | | | | | |
|---|---|---|---|---|---|
| 4,505,757 | A | * | 3/1985 | Kojima et al. | 127/36 |
| 4,774,093 | A | * | 9/1988 | Provonchee et al. | 424/493 |
| 5,455,344 | A | | 10/1995 | Harper | |
| 5,583,032 | A | * | 12/1996 | Torrence et al. | 435/91.1 |
| 5,618,850 | A | * | 4/1997 | Coury et al. | 514/772.2 |
| 5,959,096 | A | * | 9/1999 | Bennett et al. | 536/24.5 |

FOREIGN PATENT DOCUMENTS

| WO | WO 9308200 A1 | * | 4/1993 |
|---|---|---|---|
| WO | WO 94/01550 | * | 1/1994 |
| WO | WO 98/16247 | * | 4/1998 |
| WO | WO 9927086 A1 | * | 6/1999 |

OTHER PUBLICATIONS

Mathews and Van Holde "Tertiary Structure of Nucleic Acids" and "Tools of Biochemistry 21." In: Biochemistry (Benjamin/Cummings Publishing Company, Inc., 1990), pp. 99-111 and 905-908.*
Maclaughlin et al. (1998) J. Controlled Release 56:259-272.*
Sakurai et al. (2000; published online Apr. 21, 2000) J. Am. Chem. Soc. 122:4520-4521.*
Sato et al. (1996) Chemistry Lett., pp. 725-726.*
Kitamura et al. (1994) Carbohydrate Res. 263:111-121.*
Yanaki et al. (1983) Biophys. Chem. 17:337-342.*
Carter et al. (1985) J. Biol. Response Modifiers 4:495-502.*
Geiger et al. (1997) Clin. Canc. Res. 3:1179-1185.*
Saito et al. (1991) Carbohydr. Res. 18:181-190.*
Yoshioka et al. (1992) Chem. Phar. Bull. (Tokyo) 40:1221-6.*
Brown et al (In Current Protocols in Human Genetics, pp. A.3K.1-A.3K.12, 2001).*
Alkaline hydrolysis of RNA, Mantei (1998), retrieved from http://www.bio.net/bionet/mm/methods/1998-April/066485.html on Nov. 5, 2010).*
K.Sakurai, M.Mizu, S.Shinkai, *Polysaccharide-Polynucleotide Complexes. 2. Complementary Polynucleotide Mimic Behavior of the Natural Polysaccharide Schizophyllan in the Macromolecular Complex with Single-Stranded RNA and DNA, Biomacromolecules*, 2 (3), 641-650, 2001. Web Release Date: Jun. 12, 2001).
P.Midoux, et al:, *Specific Gene Transfer Mediated By Lactosylatedpoly-l-lysine Into Hepatoma Cells, Nucleic Acids Research*, Oxford University Press, Surrey, GB, vol. 21, No. 4, Feb. 25, 1993, pp. 871-878, XP000371764 ISSN: 0305-1048.
K.Ogawa, et al., *Crystal Structure Of (1->3)-Alpha-D-Glucan, ACS SYMP.* Ser. No. 141 (Fiber Diffr. Methods), 1980, pp. 353-362, XP002936532.
Olsthoorn, et al. "Circular Dichroism Study of Stacking Properties of Oligodeoxyadenylates and Polydeoxyadenylate," *Eur J Biochem* 115(2): 309-321, 1981.

* cited by examiner

*Primary Examiner* — Richard Schnizer
(74) *Attorney, Agent, or Firm* — Fay Sharpe LLP

(57) ABSTRACT

Disclosed is a gene carrier composed of a hydrogen-bonding polymer having a polymer chain with hydrogen-bonding sites formed on the polymer chain, in which the polymer chain has a conformation similar to the conformation of a nucleic acid, and particularly, the polymer chain has helix parameters similar to the helix parameters of a nucleic acid of a helix structure. In a preferred embodiment, the hydrogen-bonding polymer is composed of β-1,3-glucan such as schizophyllan. The carrier can be expected to be applied as a vector and a separator for nucleic acids because it is capable of interacting with a nucleic acid to form a complex with the nucleic acid and thus carrying the nucleic acid.

23 Claims, 4 Drawing Sheets

Molecular Ellipticity(X)

GENE CARRIER

This application is a divisional of U.S. application Ser. No. 09/889,117, filed Sep. 19, 2001 now abandoned.

TECHNICAL FIELD

The present invention relates to a gene carrier, and more particularly to a novel artificial material (compound) which is capable of interacting with a nucleic acid to form a complex with the nucleic acid for carrying the nucleic acid.

BACKGROUND ART

The analysis of the human genome is expected to be substantially completed in the early twenty-first century. For effective utilization of the outcome of the analysis, it is indispensable to develop a new technology for artificially manipulating nucleic acids (the carrying, sequence recognition, and on-off action of transcription or translation of nucleic acids). The most important material for manipulating nucleic acids is considered to be a carrier capable of supporting or carrying nucleic acids such as DNA, i.e. a gene vector. However, in-vivo use of conventional gene vectors composed of artificial materials have produced no significant results in human clinical studies. This can be attributed especially to low gene-transferring efficiency, limited expression of gene information (Cotton et al., Meth. Enzymol. 217: 618-644 (1993)), or insufficient biocompatibility of cationic carrier materials (Choksakulnimitr et al., J. Control. Rel., 32: 233-241 (1995)).

Although viruses such as retroviruses (Miller, Nature 357: 445-460 (1992)) or adenoviruses (Mulligan, Science 260: 926-932 (1993)) have shown very promising in-vitro results as gene vectors, in-vivo use of these naturally occurring materials is restricted, especially because of inflammatory action, immunogenicitic properties or the risk of integration into the genome of the viruses or mutagenesis induction due to the viruses (Crystal, Science 270: 404-410 (1995)).

Thus, as a substitute for such naturally-originating gene vectors, there has been proposed use of non-viral vectors composed of an artificial material which can be handled in an easier manner and can carry DNAs into the cells in a more efficient manner as compared with the viral vectors (Tomlinson and Rolland, J. Contr. Res., 39: 357-372 (1996)).

As materials for the transfection there have been proposed synthetic vectors based on water-soluble cationic polymers, i.e., based on the "lipofection" using cationic lipids (Gao and Huang, Gene Therapy 2: 710-722 (1995)) or amphipathic substances (Behr, Bioconjugate Chem. 5: 382-389 (1994)) Examples include the use of poly (L-lysine) (PLL) (Wu and Wu, Biotherapy 3: 87-95 (1991), DEAE-dextran (Gopal, Mol. Cell. Biol. 5: 1183-1195 (1985)), dendrimers (Haensler and Szoka, Bioconjugate Chem. 4: 372-379 (1993), or cationic methacrlylate derivatives (Wolfert et al., Hum. Gene Ther. 7: 2123-2133 (1996)). The decisive advantage of "polyfection" in which a cationic polymer is used is that almost infinite structural variations are possible which may affect physicochemical and biological properties of the polymer and that the polymer can form a complex with a plasmid. Thus, the vectors can be efficiently used when bound to cell-specific ligands such as transferrin (Qagner et al., Proc. Natl. Acad. Sci. 87: 3410-3414 (1991)), asialoglycoproteins (Wu and Wu, J. Bio. Chem. 262: 4429-4432 (1987)), antibodies (Trubetskoy et al., Bioconjugate Chem. 3: 323-327 (1992)), or carbohydrates (Midoux et al., Nucleic Acid Research 21: 871-878 (1993)).

At present, it is polyethyleneimine (PEI) that is the most extensively studied as a non-viral, artificial vector. It has been shown that PEI, a cationic polymer assuming a three dimensional branched structure in various adhesive and floating cells, may result in tranfection in a considerably highly efficient manner (Boussif et al., Gene Therapy 3: 1074-1080 (1996)). For example, 95% of in-vitro transfection with the 3T3 fibroblast cell line was accomplished. In-vivo gene transfection into mouse brain using PEI as a mediator resulted in long-term expressions of the reporter gene and Bcl 2 gene in the neuron and the glial cell, the results being comparable to those obtained with the gene transfection using the adenovirus (Aldallah et al., Hum. Gene Ther. 7: 1947-1954 (1996)).

However, the safety of cationic polymers such as polyethylimine has not yet been confirmed. While the presence of amino groups is indispensable so as to impart a cationic charge to such polymer, an amino group has a risk of toxicity in the body due to its high physiological activity. In fact, no cationic polymer studied so far has yet been put into practice, or yet been registered in the "Pharmaceutical Additives Handbook" (edited by the Pharmaceutical Additives Association of Japan and published by Yakujinipposha Publishing Co.).

Extensive studies have also been made on compounds capable of recognizing a nucleic acid sequence, such as peptide-bound nucleic acid compounds, calicheamicins (an antibiotic) and DNA-bound proteins. In addition, rapid progress has been made recently in the studies on the recognition of genes and the control of translation of genetic information by using artificial proteins. While the studies on compounds capable of interacting with nucleic acids such as DNA and RNA are being conducted as an important subject, most of the studies are directed toward unessential side issues. Few studies are found which are made based on fundamental subjects, for example, on what types of materials (compounds) will interact with a nucleic acid in general. For example, cationic materials such as polyethyleneimine, on which the current studies are being focused, are not suitable for use as an agent for carrying genes, in consideration of the facts that (1) they combine with a nucleic acid to form a complex which, once formed, will not readily decompose because of bonding due to electrostatic interaction, (2) that they are toxic, and (3) that the polycation will react with the phosphoric acid (which makes the nucleic acid water-soluble) to form a complex which is usually non-soluble. In addition, most of the compounds conventionally known undergo an irreversible reaction as an intercalater resulting in the destruction of nucleic acids (genetic information).

It is an object of the present invention to provide a new type of gene manipulator (gene carrier) which is capable of interacting with and bonding to a nucleic acid such as DNA and RNA, without destroying the nucleic acid, to form a water-soluble complex so as to be applicable under biological conditions, and which is also capable of dissociating the nucleic acid from the complex and rebonding to such nucleic acid when necessary.

DISCLOSURE OF THE INVENTION

The present invention is based on the idea arrived at by the inventors after extensive studies to accomplish the above-mentioned object, that a hydrogen-bonding polymer may be useful in carrying of genes, the isolation of nucleic acids or the regulation of the transcription and/or the translation through the interaction with a nucleic acid such as DNA and RNA to form a nucleic acid-polymer complex, in which the polymer is comprised of a polymer chain being provided hydrogen-bonding sites and having a conformation similar to the conformation of the nucleic acid.

Thus, according to the present invention there is provided a gene carrier capable of interacting with a nucleic acid to form a complex, wherein said gene carrier is composed of a hydrogen-bonding polymer having a polymer chain with hydrogen-bonding sites formed on the polymer chain, said polymer chain having a conformation similar to the conformation of the nucleic acid.

Particularly, the present invention provides a gene carrier capable of interacting with a nucleic acid of a helix structure to form a complex, wherein said gene carrier is composed of a hydrogen-bonding polymer having a polymer chain with hydrogen-bonding sites formed on the polymer chain, said polymer chain having helix parameters similar to the helix parameters of the nucleic acid.

As an example, the polymer chain having helix parameters similar to the helix parameters of the nucleic acid for use in the present invention is composed of a polysaccharide. As another example, such polymer chain is composed of a polypeptide or a synthetic polymer.

In a preferred embodiment of the present invention the hydrogen-bonding polymer is partially or wholly composed of β-1,3-glucan or β-1,3-xylan, and more preferably, β-1,3-glucan including schizophyllan, curdlan, lentinan, pachyman, griffollan or scleroglucan.

In another embodiment of the present invention there is employed hydrogen-bonding polymer in which the hydrogen-bonding sites are formed through binding a molecule or molecules having hydrogen-bonding sites to said polymer chain. In a preferred embodiment, such molecule having hydrogen-bonding sites is a monosaccharide or an oligosaccharide or is selected from guanine, cytosine, adenine, thymine, uracil or a derivative thereof.

The hydrogen-bonding polymer for composing the gene carrier of the present invention preferably has a weight-average molecular weight of 2000 or more. It is also preferred that the number of the hydrogen-bonding sites formed on the polymer chain is five or more.

Furthermore, from another aspect of the invention there is also provided a nucleic acid-polymer complex composed of a nucleic acid and a hydrogen-bonding polymer having a polymer chain with hydrogen-bonding sites formed on the polymer chain, said polymer chain having helix parameters similar to the helix parameters of the nucleic acid wherein the nucleic acid is bonded to the hydrogen-bonding polymer through the hydrogen-bonding sites.

BEST MODE FOR CARRYING OUT THE INVENTION

Figure 1:
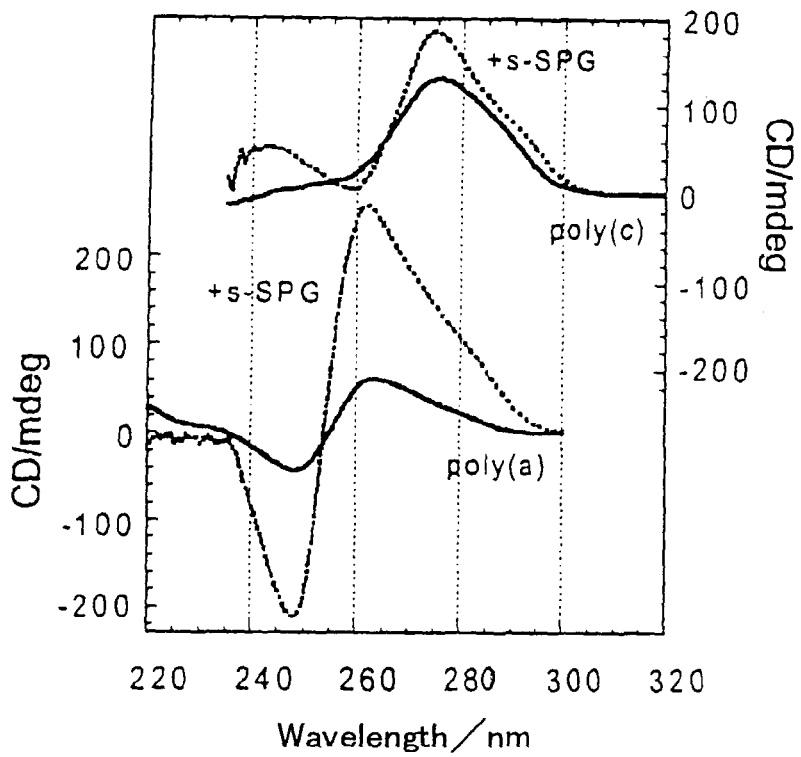
FIG. 1 is a CD spectrogram in an experiment where schizophyllan, an example of the hydrogen-bonding polymer for use as a gene carrier of the present invention, forms complexes with nucleic acids.

A gene carrier of the present invention is composed of a hydrogen-bonding polymer having a polymer chain with hydrogen-bonding sites formed on the polymer chain, in which the polymer chain has a conformation similar to the conformation of the nucleic acid. Thus, the present invention enables creation a system which is capable of interacting with nucleic acid without destroying the nucleic acid, by making use of a compound assuming a three-dimensional structure (spatial arrangement) similar to that of the nucleic acid and having sites at which the compound can bind to the nucleic acid through hydrogen bonds.

The term "hydrogen-bonding site" used with respect to the present invention refers to a functional group which can be either a proton acceptor or a proton donor. Examples of such functional groups include but are not limited to hydroxyl group, amino group, amide group, ketone, carbonyl group, urethane bond, and halogen group. The term "molecule having hydrogen-bonding sites" refers to a molecule which has such a functional group or groups as mentioned above in its molecular structure. A hydrogen-bonding polymer for composing a gene carrier of the present invention is constructed in such manner that such functional groups as mentioned above are present on its polymer chain, about which description will be given below, thus making it possible to bind the polymer to the nucleic acid (nucleic acid molecule) through hydrogen bonds.

The hydrogen-bonding polymer for composing the gene carrier of the present invention is further characterized in that the polymer chain (the main chain or skeleton) of the polymer has a conformation (spatial arrangement) which is similar to that of the targeted nucleic acid. If the targeted nucleic acid is linear, the present invention may be applied as a gene carrier for such linear nucleic acid, by using a hydrogen-bonding polymer having a polymer chain of linear conformation. However, nucleic acids mostly assume a helix structure in an aqueous solution, and the present invention is of particular significance as a gene carrier for a nucleic acid of a helix structure.

Thus, according to a particularly preferred embodiment of the present invention, there is provided a gene carrier capable of interacting with a nucleic acid of a helix structure to form a complex, wherein the gene carrier is composed of a hydrogen-bonding polymer having a polymer chain with hydrogen-bonding sites present on the polymer chain and the polymer chain has helix parameters similar to the helix parameters of the nucleic acid. As well known in the art, the term "helix parameter" is used to express the configuration of a helical compound. The helix parameters are a set of variables including the helix pitch (h), the number (R) of functional groups present per pitch, and the direction of twining (i.e. right-handed or light-handed).

The helix parameters of the polymer chain which composes the main chain or skeleton of a hydrogen-bonding polymer for the present invention is determined depending upon the type of a nucleic acid with which the polymer interacts to form a complex. For the formation of a complex with a nucleic acid, while the polymer chain must have the same twining direction as the nucleic acid, complete coincidence is not indispensable and near values suffice for the remaining variables, h and R. Thus, it suffices that the polymer chain of the hydrogen-bonding polymer have helix parameters similar to those of the nucleic acid, in an aqueous solution. In view of the fact that the h/R (pitch per functional group) values of nucleic acids generally reside in the range of 2 to 4 Å, a criterion for allowable similarity will be that the polymer chain has an h/R value, preferably in the range of 2 to 4 Å, more preferably in the range of 2.4 to 3.6 Å as in single-stranded nucleic acid in general, and far more preferably, in the range of 2.4 to 3.3 as in most single-stranded nucleic acids.

The values for the helix parameters of various helical compounds including nucleic acids and polymers are easily available from a number of literature references. For example, from "Principles of Nucleic Acid Structure" by W. Saenger (published in 1987, by Springer Verlag Tokyo), it is known: h=28.2 Å, R=11, and right-handed for A-type DNA; h=18.6 Å, R=6, and right-handed for poly(C), a synthetic RNA. In the present invention it is essential to use a polymer chain having helix parameters similar to those of a nucleic acid, because the use of such polymer chain makes it easier thermodynamically to form a complex with the nucleic acid. For example, as detailed in the Examples given later, the helix parameters of polysaccharide composed of β-1,3-glucan as the main chain is very close to that of Poly(C), as described in "Takahashi, Kobata and Suzuki, Prog. Polym. Phys. Japan, Vol. 27, p 767", or "Conformation of Carbohydrates, Harwood Academic Publisher, 1998". Thus, a polysaccharide having β-1,3-glucan as the main chain, such as schizophyllan, lentinan, and curdlan, can easily form a complex with the nucleic acid. If the helix parameter values are unknown, they can be obtained from crystallographic analysis data, because the local conformation of a polymer in a solution is reflected in crystallographic structure. For example, it is possible to obtain helix parameter values by analyzing such data as light scattering, limiting viscosity and NMR data, in such manner as described in "Helical Wormlike Chains in Polymer Solutions, H. Yamakawa, Springer Verlag, 1997".

Preferred examples of the polymer chain having helix parameters similar to those of a nucleic acid of a helix structure are polysaccharides such as β-1,3-glucan and β-1,3-xylan. When a polysaccharide such as β-1,3-glucan or β-1,3-xylan is employed, not only is the polysaccharides composed of a "polymer chain having helix parameters similar to those of a nucleic acid" but it also intrinsically has "hydrogen-bonding sites" on the polymer chain. Thus, there is no need to bind "a molecule or molecules having hydrogen-bonding sites" to the polymer chain. It also suffices for β-1,3-glucan or β-1,3-xylan to compose part of a hydrogen-bonding polymer.

A particularly preferred example of the hydrogen-bonding polymer for use in the present invention is β-1,3-glucan. Various types of β-1,3-glucan are known by customary names such as schizophyllan, curdlan, lentinan, pachyman, griffollan and sucleroglucan. All these glucans are naturally occurring polysaccharides composed of a main chain connected through β-bonds (β-D-bonds) with different frequencies of side chains. The solubility of any such polysaccharide can be controlled by properly thinning out the side chains by the conventional periodate method. Interestingly, as described in the Examples given later, unlike β-1,3-glucan to be used in the present invention, neither a polysaccharide composed of glucopyranose in which the main chain is connected through α-D-bonds nor a polysaccharide such as 1,4-glucan which is composed of a main chain connected through β-D-bonds but has helix parameters different from those of a nucleic acid, is capable of forming a complex with a single-stranded DNA or RNA.

A β-glucan such as schzophyllan generally assumes a triple helix structure in water, and is therefore dissolved in a solvent such as DMSO (dimethyl sulfoxide) thereby making it a single-strand when used as a gene carrier according to the present invention. When an aqueous solution (or a polar solvent solution such as an alcohol solution) containing the targeted DNA or RNA is added, there occur intramolecular and intermolecular associations among the polysaccharide molecules due to the hydrophobic interactions. The single-stranded DNA or RNA molecules are taken into the associated polysaccharide molecules thereby forming a nucleic acid-polysaccharide complex.

As a polymer chain having helix parameters similar to those of a nucleic acid for use in the present invention, there can be used various types of polypeptides or synthetic polymers, in addition to the above-mentioned polysaccharides. Examples include but are not limited to polypeptides having a (2-aminoethyl) glycine skeleton or (3-aminopropyl) glycine skeleton, and synthetic polymers such as polyisocyanates and polymethylmetharylates.

When these peptides or synthetic polymers are composed of a polymer chain having helix parameters similar to those of a nucleic acid but do not have hydrogen-bonding sites, it is necessary to make them a hydrogen-bonding polymer by binding a molecule or molecules having hydrogen-bonding sites to the polymer chain thereby forming hydrogen-bonding sites on the polymer chain. For example, when a polypeptide having a (2-aminoethyl) glycine skeleton or (3-aminopropyl) glycine skeleton is used as a hydrogen-bonding polymer according to the present invention, it is necessary to arrange a "molecule having hydrogen-bonding sites" on the polymer chain since the polymer chain of such polypeptide per se has no hydrogen-bonding ability.

As a molecule having hydrogen-bonding sites, there can be used various types of molecules having functional group or groups which can be either a proton acceptor or a proton donor as described above. It also suffices for hydrogen-bonding sites composed of different types of functional groups to be present in a single molecule. In this respect, a monosaccharide or an oligosaccharide is particularly suitable as the molecule having hydrogen-bonding sites, because such saccharide has a plurality of hydroxyl and amino groups in a single molecule. Examples of such molecules include but are not limited to glucose, galactose and mannose. As a molecule having hydrogen-bonding sites, there can also be used a nucleic acid base such as guanine, cytosine, adenine, thymine, uracil or a derivative thereof.

By binding the monosaccharide, oligosaccharide or nucleic acid base to the polymer chain as described above, there can be obtained a hydrogen-bonding polymer for use as a gene carrier of the present invention. This can be accomplished by binding the reducing group terminals of such saccharide to the functional groups on the polymer chain, optionally using a spacer molecule. As such spacer, there can be used a bifunctional compound such as ethylene glycol or an amino acid. A compound which intrinsically has the polymer chain as well as the hydrogen-bonding sites can also be used.

A hydrogen-bonding polymer for composing the gene carrier of the present invention may be chemically modified if necessary. For example, for increased affinity with cell membranes, the polymer may be bound with lipids. Examples of such lipids include steroids such as cholesterol, fatty acids, triacyl glycerol, fats, and phospholipids. For cell recognition, a glycocalix or a glycolipid may be combined. For improving binding with nucleic acids, polycations, such as polylysine or polyethylimine, may be bound to the polymer so that they will combine to anionic sites of nucleic acids. It also suffices for the polymer to be bound with a nucleic acid base such as guanine, cytosine, adenine, thymine, uracil or a derivative thereof.

The length (or molecular weight) of the hydrogen-bonding polymers for use as the gene carriers of the present invention may vary depending upon the purpose of using the polymer. However, a polymer having too small molecular weight is not preferable, because the so-called cluster effect (the cooperativity in a polymer system) will not readily occur. For the formation of a complex with the nucleic acid, the polymer should have a weight-average molecular weight of preferably 2000 or more, more preferably 4000 or more, most preferably 6000 or more, although the optimum value depends upon the type and the high-order structure of the nucleic acid. The "hydrogen-bonding sites" formed on the polymer should be in such number as necessary for the formation of a complex with a nucleic acid. The number should be five or more, preferably eight or more, more preferably ten or more, although the optimum number may depend upon the type and the high-order structure of the nucleic acid.

Thus, a hydrogen-bonding polymer as described above is capable of interacting with a nucleic acid such as DNA or RNA to form a complex with the nucleic acid, in which the binding capability of the hydrogen-bonding polymer to the nucleic acid may vary depending upon the chemical structure of the nucleic acid or gene (type of nucleic acid base (A, T, G, C, U) or the nucleic acid sequence). The formation of the complex can be confirmed by studying the conformational change, for example, by measuring the CD (circular dichroism) spectra. The complex thus obtained according to the present invention is generally water-soluble. In addition, the complex may dissociate and undergo a rebinding, due to temperature change and/or pH change. Furthermore, the complex has resistance to nuclease, resulting in no destruction of nucleic acids (genes).

Thus, the gene carrier composed of the hydrogen-bonding polymer of the present invention is capable of carrying a targeted gene (DNA, RNA), in the form of a nucleic acid-polymer complex, which can be injected into the body or tissue cultures. The present invention can therefore be expected to contribute to the development of medicines and reagents for diagnostic or therapeutic purposes. The gene carrier of the present invention may also be utilized as a nucleic acid-protecting agent since it has resistance to nuclease through the formation of a complex with the nucleic acid. In addition, the gene carrier of the present invention may be applied as a separating agent for nucleic acids by making use of its difference in binding ability to various nucleic acids.

The hydrogen-bonding polymer according to the present invention may be subjected to a required chemical modification when it is put into practical use as a gene vector. The chemical modification may be carried out by a well-known method, for example, by the reduction-amination method or the introduction of glycosyl-bonds. For improved cell membrane permeability, it may be necessary to introduce a small quantity of cations. For example, periodate selectively cleaves the 1,2 diols of β-1,3-glucan resulting in the formation of two aldehydes. The main chain of schzophyllan or lentinan includes no sites which may undergo such cleavage. Thus, through the aldehyde groups, the desired substituent groups can be introduced only into the side chains of the β-1,3-glucan.

When the hydrogen-bonding polymer of the present invention is intended for use as an agent for separating nucleic acids or genes, it is necessary that the polymer should be gelated or supported on the surface of a matrix material. For example, the gelation of β-1,3-glucan can be carried out by the known method (see, for example, Polymer. J. Vol. 31, p 530 and literature references cited therein). Schizophyllan can be supported on a matrix by reacting the functional group-bound schizophyllan as mentioned above with a reactive gel.

EXAMPLES

The invention will be more fully described with reference to the following examples, which are only for exemplifying purposes and not for restricting the invention.

Example 1 through Example 3 are for showing that β-1,3-glucan (schizophyllan) forms a complex with a nucleic acid (RNA) and functions as a gene carrier. Example 4 gives the values for helix parameters of schizophyllan as used in Examples 1 to 3 and other polysaccharides in comparison with those of certain nucleic acids, indicating that there should be a similarity in helix parameters for the formation of the complex. This Example also shows the results of experiments in which the hydrogen-bonding polymer formed the complexes with the nucleic acids. Example 5 shows the preparation of schizophyllan which is bound with fluoresceine, a fluorochrome, as an example of the chemically modified hydrogen-bonding polymer, and also shows its capability to form the complex. Example 6 shows the influence of the molecular weight of schizophyllan, a hydrogen-bonding polymer of the invention, on the formation of a complex with the nucleic acid.

Example 7 shows the synthetic preparation of a hydrogen-bonding polymer which is composed of (2-aminoethyl) glycine, as a polymer chain having helix parameters similar to a nucleic acid, and glucose, as a molecule having hydrogen-bonding sites. This Example also shows experimental results in which the polymer formed a complex with the nucleic acid. Example 8 shows experimental results in which a nucleic acid-polymer complex of the present invention had resistance to nuclease, suggesting a possible application of such complex. Example 9 is an example of experiments showing that the gene carrier composed of the hydrogen-bonding polymer (schizophyllan) of the present invention functions as a gene vector which regulates the expression of a protein. Example 10 is an example of experiments showing that the gene carrier composed of the hydrogen-bonding polymer (schizophyllan) functions as an agent for separating nucleic acids. Example 11 shows an experiment in which the properties of the hydrogen-bonding polymer for composing the gene carrier of the present invention were changed. Example 12 is an example of experiments showing that the gene carrier composed of the hydrogen-bonding polymer (schizophyllan) of the present invention is capable of forming a complex with a nucleic acid and also that such complex may be dissociated in the presence of complementary chains. Finally, Example 13 is an example of experiments showing that the gene carrier composed of schizophyllan of the present invention is capable of forming a complex with a nucleic acid (DNA) and carrying the nucleic acid.

Example 1

Schizophyllan of a triple helix structure was prepared as follows by the conventional method as described in "A. C. S. 38(1), 255 (1997); Carbohydrate Research, 89, 121-135 (1981)): *Schizophyllum commune*. Fries (ATCC 44200) available from American Type Culture Collection was subjected to a stationary culture in a minimal medium for seven days. After removal of the cellular materials and insoluble residues, the supernatant was subjected to a supersonic treatment to yield schizophyllan of a triple helix structure having a molecular weight of 450000.

The schizophyllan was dissolved in a DMSO solution (1%), thereby unbinding the triple helix into a single strand. The solvent was replaced with water by means of ultrafiltration. The concentration of schizophyllan was adjusted to be 0.5 g/dL. To 100 microliter of this solution, there were added 1000 microliter of pure water (pH 6.5) and 100 microliter of a nucleic acid solution containing poly(A) (0.1 g/dL). The resultant solution was opaque and homogeneous.

Example 2

A mixture was prepared in the same manner as in Example 1, except that schizophyllan of a triple helix structure having a molecular weight of 70000 was used. The resultant solution was opaque and homogeneous.

Example 3

A mixture was prepared in the same manner as in Example 1, except that poly(C) was used in place of poly(A). The resultant solution was opaque and homogeneous.

Comparative Examples 1 to 4

Mixtures were prepared in the same manner as in Example 1, except that polyethylimine (Aldrich), pullulan (main chain α-1,6-bonds), dextran (main chain: α-1,6-bonds) and amylose (main chain α-1,4-bonds) were respectively used in place of schizophyllan. The resultant solutions were opaque, except for the solution with polyethylimine, which was turbid.

The CD spectra of all the solutions prepared in the above-mentioned Examples and Comparative Examples were measured using a circular dichroism apparatus (JASCO) to confirm the formation of a complex.

Figure 2:
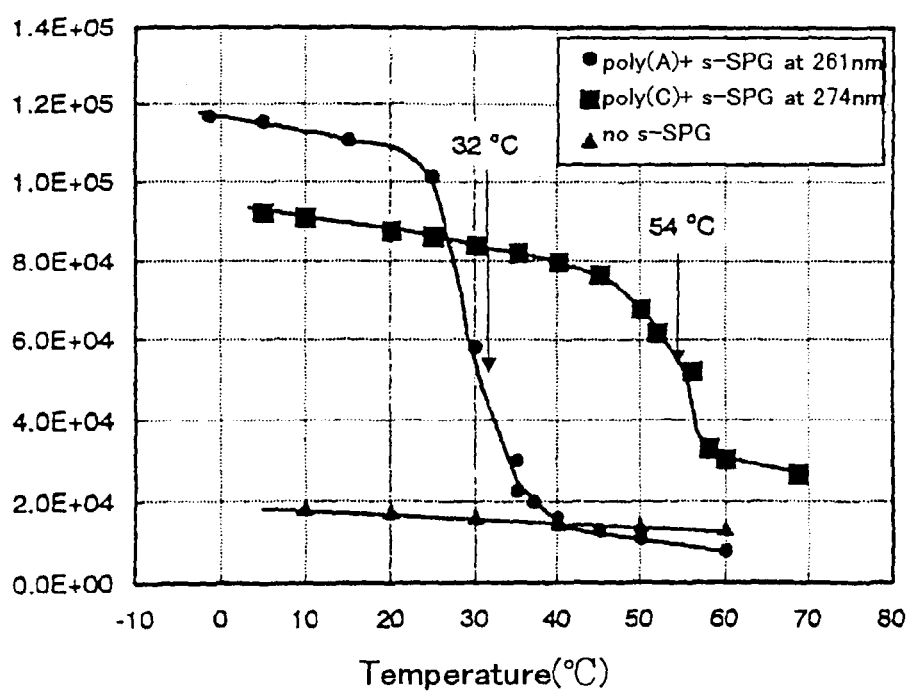
FIG. 2 illustrates temperature dependency of the CD spectra in an experiment where schizophyllan, an example of the hydrogen-bonding polymer for use as a gene carrier of the present invention, forms complexes with nucleic acids.

FIG. 2 shows the CD spectrum data for Example 2 and Example 3 In the figure, ● denotes the CD spectrum in the case where poly(A) was used (Example 2), ■ the CD spectrum in the case where poly(C) was used (Example 3), and ▲ the CD spectrum of poly(C) only, without the addition of schizophyllan. In the figure, s-SPG denotes the single-stranded schizophyllan.

As seen from the plots of ●, there was a sharp change in the CD spectrum at around 30° C., indicating that poly(A) was dissociated from the complex at 32° C. As seen from the plots of ■, there was a sharp change in the CD spectrum at around 50° C., indicating that poly(C) was dissociated from the complex at 54° C. There was no such change in the CD spectrum in the case where schizophyllan was not used (▲).

The results of the CD measurements are summarized in Table 1.

TABLE 1

| Example | Model Gene | Polymer | Complex Formation at 5° C. | Complex Formation at 50° C. |
|---|---|---|---|---|
| Example 1 | Poly(A) | Schizophyllan | Formed | Dissociated |
| Example 2 | Poly(A) | Schizophyllan | Formed | Dissociated |
| Example 3 | Poly(C) | Schizophyllan | Formed | Dissociated |
| Com. Example 1 | Poly(A) | Polyethylimine | Formed, Precipitated | Formed, Precipitated |
| Com. Example 2 | Poly(A) | Pullulan | Not Formed | Not Formed |
| Com. Example 3 | Poly(A) | Dextran | Not Formed | Not Formed |
| Com. Example 4 | Poly(A) | Amylose | Not Formed | Not Formed |

Table 1 shows that, in the cases where schizophyllan was used according to the present invention, there was formed a water-soluble complex at 5° C. and such complex was decomposed at 50° C., By contrast, polyethylimine (Comparative Example 1) formed an insoluble complex which precipitated. None of the polysaccharides used in Comparative Examples 2 to 4 formed a complex.

Example 4

Figure 3:
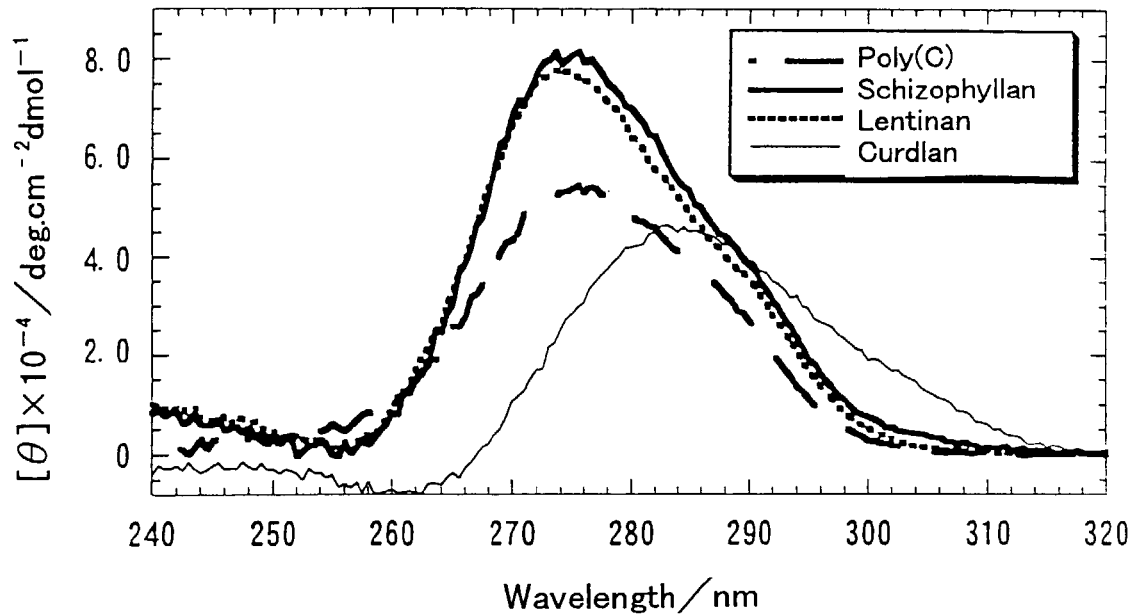
FIG. 3 is a CD spectrogram in an experiment where polysaccharides, the hydrogen-bonding polymers for use as gene carriers of the present invention, form complexes with nucleic acids.

Comparison was made of the helix parameters of schizophyllan as used in Example 1 to 3 and other polysaccharides (lentinan, curdlan, β-1,3-xylan, amylose, and cellulose) with those of nucleic acids [A-DNA, B-DNA, poly(A) and poly(C)]. The helix parameter values for these compounds were acquired by reference to the literature references mentioned previously. A mixture of each polysaccharide with poly(C) was prepared in the same manner as in Example 1, for the CD spectrum measurement to confirm the formation of the complex. The results are given in Table 2 and FIG. 3. These results show that for the formation of a complex with a nucleic acid there must be a similarity in the helix parameters to those of the nucleic acid, as in the case of β-1,3-glucan (schizophyllan, lentinan, curdlan) and β-1,3-xylan.

TABLE 2

| Sample | Direction of Twining | Helix pitch h(Å) | Number of Residues R | h/R (Å) | Complex Formation |
|---|---|---|---|---|---|
| A-DNA | Right-handed | 28.2 | 11.0 | 2.56 | |
| B-DNA | Right-handed | 33.8 | 10.0 | 3.38 | |
| Poly(A) | Right-handed | 25.4 | 9.0 | 2.83 | |
| Poly(C) | Right-handed | 18.6 | 6.0 | 3.10 | |
| Schizophyllan | Right-handed | 17.4 | 6.0 | 2.90 | Yes |
| Lentinan | Right-handed | 17.4 | 6.0 | 2.90 | Yes |
| Curdlan | Right-handed | 17.4 | 6.0 | 2.90 | Yes |
| β-xylan | Right-handed | 18.0 | 6.0 | 3.00 | Yes |
| Amylose | Right-handed Left-handed | 8.0 | 6.0 | 1.33 | No |
| Cellulose | Right-handed | 10.3 | 2.0 | 5.15 | No |

Example 5

Schizophyllan having a molecular weight of 450000 as used in Example 1 was dissolved in ion-exchanged water to prepare 10 ml of 1 wt % aqueous solution. Fluorescein-4-isothiocyanate (Dojin Chemicals Co., Cat. No. FITC-1) was dissolved in acetone (dehydrated by distillation in the conventional manner) to prepare a 5 wt % solution. Two ml of this solution of fluorescein in acetone was added to the aqueous solution of schizophyllan under vigorous stirring. After stirring for an hour at room temperature, the reaction solution was added into a large volume of methanol, from which the precipitated schizophyllan was recovered. The recovered shizophyllan was subjected to several cycles of dissolving-in-water and reprecipitation-from-acetone operations. The resultant saccharide was tinged with yellowish green. There was no change in the limiting viscosity in water. No change was observed in the saccharide peak with a proton NMR in DMSO. From the UV absorption coefficient, the quantity of fluorescein was estimated to be 2 to 7 per 1000 repeating units of schizophyllan.

The fluorescein-modified schizophyllan thus obtained was measured for circular dichroism (CD) spectrum in the same manner as in Example 1 and the formation of a complex was confirmed.

Example 6

Figure 4:
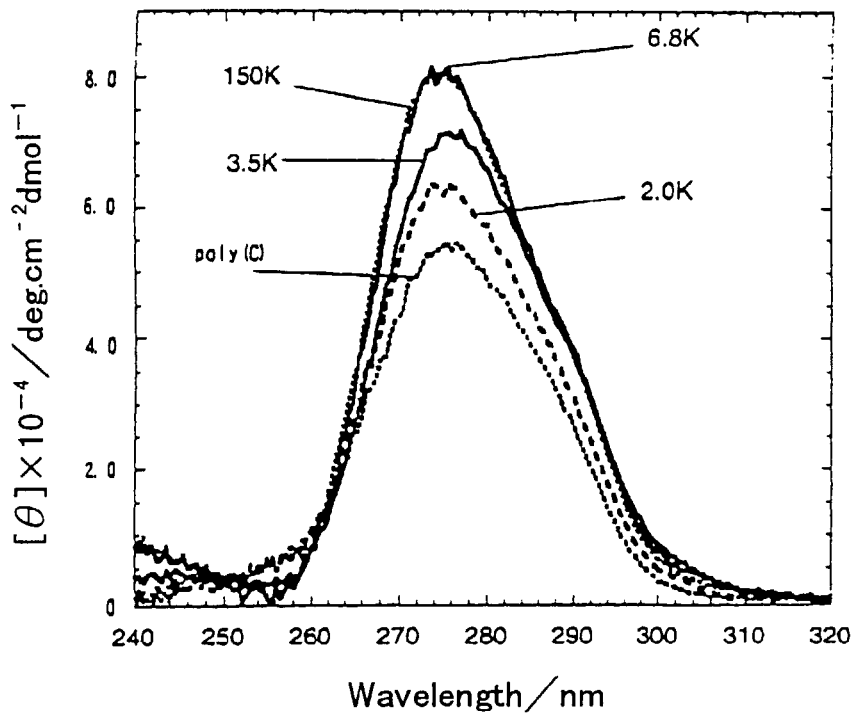
FIG. 4 is a CD spectrogram which indicates the effect of the molecular weight of schizophyllan on the formation of a complex with the nucleic acid.

CD spectrum measurements were made to study the influence of the molecular weight of schizophyllan, an example of the hydrogen-bonding polymer, on the formation of a complex with poly(C), a nucleic acid. The results are shown in FIG. 4. As can be seen from FIG. 4, the formation of the complex with the nucleic acid was promoted with increasing the molecular weight, but such effect saturated beyond a certain value of the molecular weight.

Example 7

Figure 5:
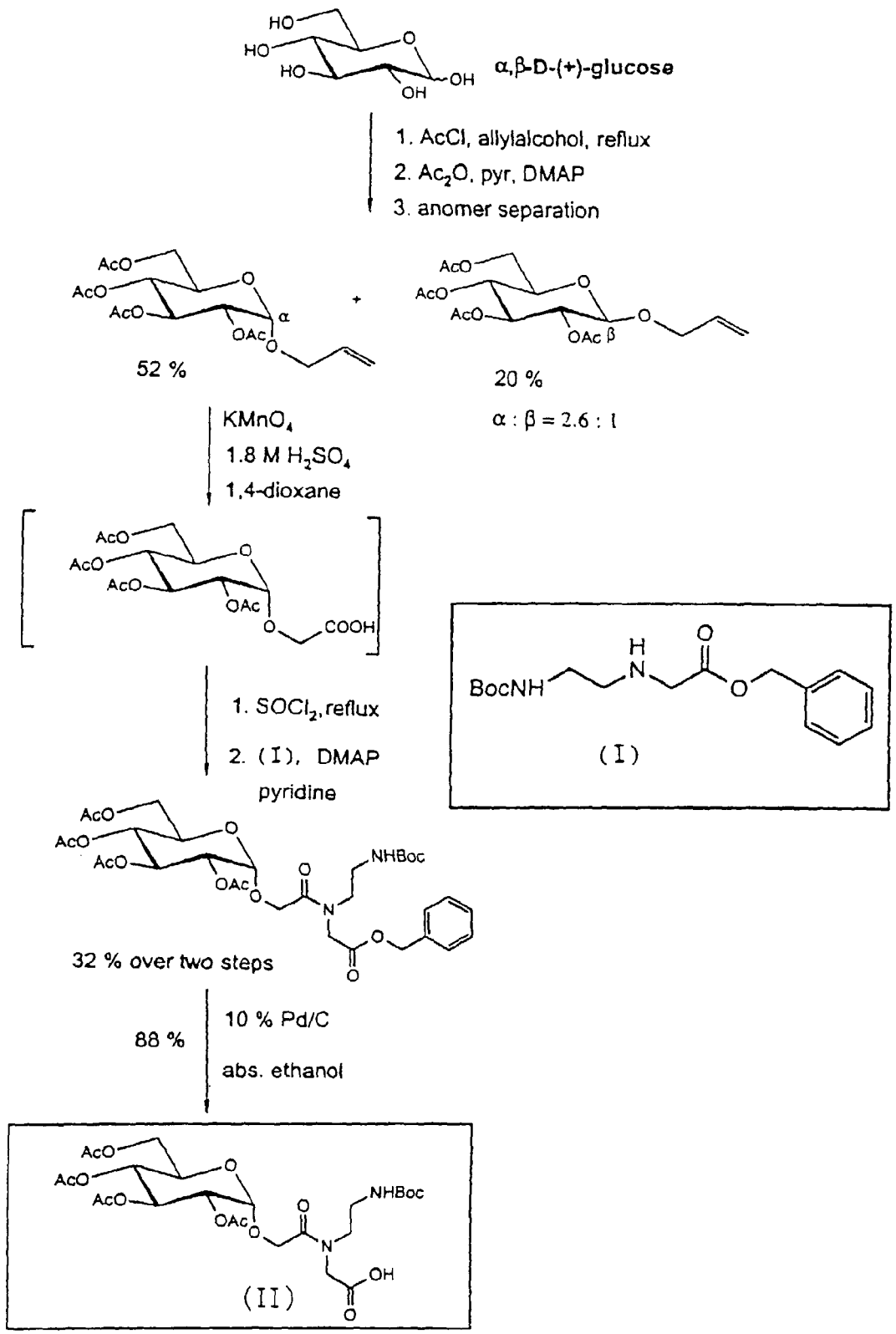
FIG. 5 shows a reaction scheme for synthesizing the saccharide-bound N-(2-aminoethyl) glycine derivative from which is prepared the saccharide-bound polyamino acid, an example of hydrogen-bonding polymer for use as a gene carrier of the present invention.

An N-(2-aminoethyl)glycine derivative was synthesized from ethylene diamine through the well-known synthetic route (see, for example, E. Uklman et al., Angew. Chem., 1998, 110, 2954-2983). The yield was about 60%. Using glucose as a molecule having hydrogen-bonding sites, the N-(2-aminoethyl)glycine derivative (I) was modified with glucose to produce the compound (II), in the manner described in FIG. 5. From the compound (II), there was synthesized polyamino acid modified with glucose and having fifteen repeating units, by the conventional amino acid polymerization method (the Merrifield method).

The helix parameter values for this polymer, calculated from the MOPAC based on molecular force field, were as follows: right-handed, h=10-20 Å, and R=4-7.

This polyamino acid modified with the saccharide was measured for the capability of forming a complex in the same manner as in Example 1, and, as a result, there was observed a ten percent increase in the CD spectrum peak intensity, indicating the formation of the complex.

Example 8

Schizophyllan as used in Example 1 was dissolved in DMSO. To the resultant solution, there was added a poly(C) solution in a tris buffer. In the presence of RNase-A (Nippon Gene Co.) at a concentration of $10^{-4}$ g/L, the hydrolysis rate of poly(C) was determined through the absorption spectra and by liquid chromatography. The final concentration of the schizophyllan was adjusted to be $6.6 \times 10^{-4}$ M and the volume fraction of water was adjusted to be 0.9, with the concentration of poly(C) being varied in the range of $0.5 \times 10^{-4}$ M to $3.5 \times 10^{-4}$ M. The hydrolysis rate was also determined in the same manner in the absence of the schizophyllan, as a reference.

Comparative Example 5

The hydrolysis rate of poly(C) was determined through the absorption spectra and by liquid chromatography, in the same manner as in Example 8, except that the schizophyllan was replaced with the same weight of polyethyleneimine (Wako Pharmaceuticals, molecular weight: 1000) The analysis by liquid chromatography indicated the formation of the monomer and the dimer, which increased as time elapsed.

Figure 6:
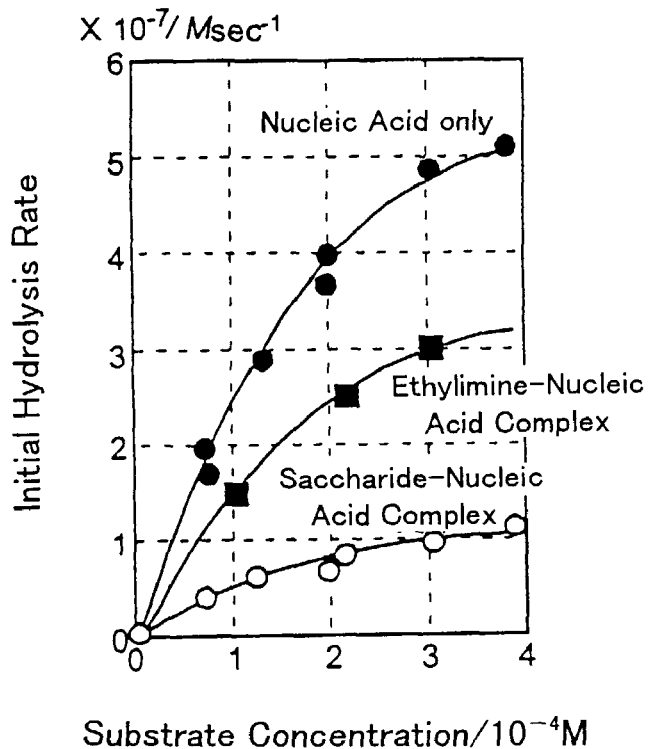
FIG. 6 a graphical representation of the experimental results showing that the nucleic acid-polymer complex according to the present invention has resistance to a nuclease.

FIG. 6 shows the dependencies of the initial hydrolysis rates, calculated from the absorption spectrum changes, upon the substrate concentration (the concentration of the base of poly(C)). The hydrolysis rate in the case of the nucleic acid only (the reference) is much higher than that in the case where the schizophyllan was added. In addition, the hydrolysis rate in the case of the addition of polyethyleneimine (which has conventionally been known as an excellent suppressor to the hydrolysis of a nucleic acid) is also higher than that in the case where the schizophyllan was added, indicating that the schizophyllan-nucleic acid complex protects the nucleic acid from the nuclease more effectively than the polyethyleneimine-nucleic acid complex does.

Example 9 and Comparative Example 6

An in-vitro experiment was carried out utilizing a well-known system, in which GFP (Green Fluorescence Protein), a fluorescent protein, is to be expressed as a reporter in *E. coli*. T7S30, a cellular extract. T7 promoter gene (CTTTAA-GAAGGAGATATACC; SEQ ID NO:1) was selected as the target gene to be blocked. Thus, an antisense DNA was constructed by linking a sequence (GGTATATCTCCTTCT-TAAAG; SEQ ID NO:2), which is complementary to the targeted gene sequence, with thirty dAs at the 5' end thereof. The measurements for fluorescence intensity were expressed in terms of relative fluorescence intensities in which the value for the fluorescence intensity in the absence of the antisense DNA was 100. SPG (schizophyllan) was added to the antisense DNA in the same manner as in Example 1, while successively increasing the moles of the schizophyllan with respect to the antisense DNA, i.e., 0.5, 1.0, 2.0, and 10 times (Example 9). For comparison, polyethylimine (PEI) was also added to the antisense DNA in the same manner as in Example 1, while successively increasing the moles of PEI with respect to the antisense DNA, i.e., 0.5, 1.0, 10 and 100 times (Comparative Example 6). The results are shown in FIG. 7.

Figure 7:
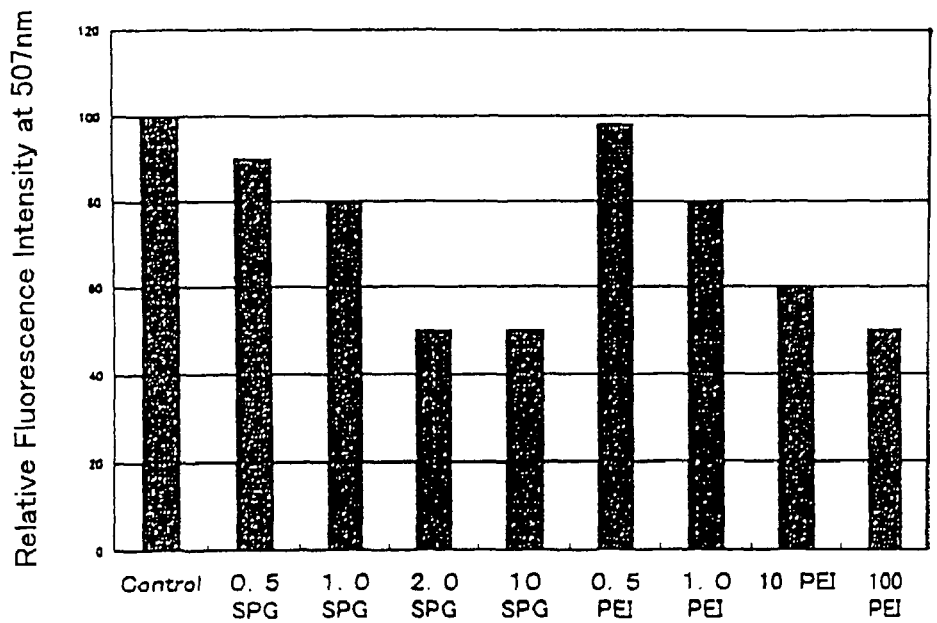
FIG. 7 a graphical representation of the experimental results showing that the hydrogen-bonding polymer according to the present invention functions as a gene vector.

As shown in FIG. 7, the fluorescence intensity due to the expression of GFP decreased as the amount of SPG or PEI added increased, indicating that there were formed complexes of the antisense DNA with SPG or PEI, which suppressed the translation and transcription of the reporter gene, GFP. With SPG, it was found that the effect of suppression was not enhanced any more when added in amounts of two or more times in moles. This is probably because the complex is formed stoichiometrically and an addition of SPG in an amount exceeding that for the complex formation has no effect. Comparing two cases in which 10 times in moles of SPG and PEI were added, PEI was less effective in the suppression than SPG, indicating the superiority of SPG according to the present invention over PEI. A decrease in the fluorescence was observed when 100 times in moles of PEI was added. As is known, this is probably caused by the cytotoxity due to the excessive amount of PEI added. By contrast, schizophyllan is believed to exhibit almost no toxicity since there was observed no significant decrease in the fluorescence intensity when added in such a high amount as 100 times in moles.

Example 10

To 400 mg (wet weight) of AF-Amino TOYOPEARL 650M (TOSOH), there were added 50 mg ($3.3 \times 10^{-7}$ mol) of schizophyllan (molecular weight: 2000), 100 mg ($1.6 \times 10^{-3}$ mol) of cyanoborohydride sodium and 1.0 ml of aqueous solution of potassium dihydrogenphosphate (0.2N). The resultant mixture was stirred for 38 hours at 60° C. under shaking, and the residue was washed with distilled water (20 ml), borate buffer (pH 9.18) (20 ml), and distilled water (20 ml), followed by the addition of 0.3 ml of aqueous solution of sodium acetate (0.2N) and 0.2 ml of acetic anhydride. The mixture was kept at 25° C. for 30 minutes, and then the residue was washed with distilled water (50 ml), sodium hydroxide (0.1N) (50 ml) and distilled water (50 ml).

The resultant was then packed in a column of 3 cm length and 2 mm radius. An aqueous solution (pH 6) containing poly(A) and poly(U), each in a concentration of 0.1 wt %, was passed through the column while the column was kept in a thermostat at 5° C. The concentrations of the nucleic acids in the effluent solution were measured with an ultraviolet absorption spectrometer. While there was observed no change in the concentration of poly(U) within the error limits, the concentration of poly(A) in the effluent solution was found to be less than 0.05 wt %. Then, the column was washed with a sufficient amount of water. On passing an aqueous solution (pH=4) through the column, the presence of poly(A) was detected in the effluent. Thus, it was confirmed by this Example that schizophyllan as used in the present invention is capable of separating RNA.

Example 11

300 mg of schizophyllan was dissolved in 300 ml of water, followed by the addition of a periodate solution in water. The resultant mixture was stirred for two days in a refrigerator. The solution was subjected to dialysis to remove the periodate, followed by a lyophilization. The resultant white solid material was dissolved in DMSO, followed by the addition of an excessive amount of an amine or hydrazine derivative. The mixture was stirred for two days at room temperature, and then added with sodium borohydride, followed by stirring for one day at room temperature. After deactivating the excess sodium borohydride with acetic acid, the mixture was subjected to dialysis against a weak acid aqueous solution, a basic aqueous solution and then distilled water, followed by lyophilization to yield the desired compound.

The compound was evaluated for the degree of introduction of amino groups, by the method described in "Biochemistry, Vol. 6, No. 2, p 541". It was found that there were two amino groups introduced per 100 side chains. The schizophyllan thus obtained was allowed to react with poly(C) on poly(A) to form a complex, in the same manner as in Example 1, and then an experiment was carried out in the same manner as described in FIG. 2. As a result, it was found that the temperatures at which the complexes decomposed were approx. 10° C. higher than those (as shown in FIG. 2) in the case where the schizophyllan was not introduced with amino groups.

Example 12

A 1200 microliter mixture of schizophyllan and poly(A) was prepared in the same manner as described in Example 1. A poly(U) solution was also prepared by adding poly(U), which was equimolar to the poly(A) in said mixture, to 1200 microliter of 0.4M sodium chloride aqueous solution. The poly(U) solution thus prepared was added dropwise to the schizophyllan-poly(A) mixture. The resultant mixture was kept at 100° C. for three hours, and then measured for CD spectrum. The CD spectrum showed the formation of the well-known double-helix structure of poly(A)-poly(C).

The ultraviolet absorption spectrometry also indicated an absorption coefficient value which is typical for a poly(A)-poly(U) double helix (see, for example, Experimental Chemistry Series, "Nucleic Acid II"). Thus, on addition of the poly(U), the schizophyllan-poly(A) complex decomposed to form a new complex composed of poly(A) and poly(U). This Example therefore demonstrates that the presence of complementary chains promotes hybridization reactions.

Example 13

A mixture of schizophyllan and poly(dA) and a mixture of schizophyllan and poly(dT), each in a volume of 1200 microliter, were prepared in the same manner as in Example 1. With both of these mixtures, CD spectrum measurements showed the formation of a complex. Thus, schizophyllan is capable of forming a complex with DNA as well as RNA, and can be a carrier for these nucleic acids.

The invention claimed is:

1. An isolated nucleic acid-polymer complex composed of a bonded nucleic acid and a hydrogen bonding polymer having a polymer chain comprising a naturally occurring β-1,3-glucan with hydrogen-bonding sites on the polymer chain, said hydrogen bonding sites being formed on said polymer chain by unbinding a β-1,3-glucan to form a single stranded β-1,3-glucan capable of forming a complex with a single stranded nucleic acid, said single stranded nucleic acid comprising a poly(dA), poly(A), or poly(C) nucleic acid and, when being combined with the single stranded β-1,3-glucan, said poly(dA), poly(A), or poly(C) nucleic acid being a helical compound, and said polymer chain, when in aqueous solution, having helix parameters similar to the helix parameters of the poly(dA), poly(A), or poly(C) of the single stranded nucleic acid, the similar helix parameters including an h/R value in a range of 2 to 4 Å, wherein the bonded nucleic acid is bonded to the hydrogen bonding polymer through the hydrogen-bonding sites.

2. The nucleic acid polymer complex of claim 1, wherein the naturally occurring β-1,3-glucan is schizophyllan.

3. The nucleic acid polymer complex of claim 1, wherein the bonded nucleic acid comprises RNA or DNA.

4. The nucleic acid polymer complex of claim 1, wherein the β-1,3-glucan is curdlan, lentinan, pachyman, griffollan or sceroglucan.

5. The nucleic acid polymer complex of claim 1, wherein the hydrogen-bonding polymer has a weight-average molecular weight of 2000 or more.

6. The nucleic acid polymer complex of claim 4, wherein the wherein the hydrogen-bonding polymer has a weight-average molecular weight of 6000 or more.

7. An aqueous solution comprising the nucleic acid-polymer complex of claim 1.

8. A method of forming an isolated nucleic acid-polymer complex composed of a bonded nucleic acid and a hydrogen bonding polymer having a polymer chain comprising a β-1,3-glucan with hydrogen-bonding sites on the polymer chain, comprising:
   unbinding a triple helix structure comprising a naturally occurring β-1,3-glucan to form a single stranded β-1,3-glucan comprising a hydrogen bonding polymer having a polymer chain with hydrogen-bonding sites formed on the polymer chain; and
   combining the hydrogen bonding polymer with an aqueous solution of a single stranded nucleic acid comprising poly(dA), poly(A), or poly(C) to form the complex, said polymer chain, when in said aqueous solution, having helix parameters similar to the helix parameters of the poly(dA), poly(A), or poly(C) of the single stranded nucleic acid, wherein said poly(dA), poly(A), or poly(C) of the single stranded nucleic acid and the hydrogen bonding polymer are helical compounds, the similar helix parameters including an h/R value in a range of 2 to 4 Å, whereby the bonded nucleic acid is bonded to the hydrogen bonding polymer through the hydrogen-bonding sites.

9. The method of claim 8, wherein the β-1,3-glucan is schizophyllan.

10. An isolated nucleic acid-polymer complex composed of a nucleic acid and a hydrogen bonding polymer having a polymer chain with hydrogen-bonding sites on the polymer chain, wherein the nucleic acid is bonded to the hydrogen bonding polymer through the hydrogen-bonding sites, said polymer chain having a twining direction which is the same as that of the nucleic acid, the hydrogen bonding polymer being partially or wholly composed of a naturally occurring β-1,3-glucan and the nucleic acid being bonded comprising a single-stranded nucleic acid comprising poly(dA), poly(A), or poly(C) residues, the poly(dA), poly(A), or poly(C) residues forming a helical compound.

11. The nucleic acid polymer complex of claim 10, wherein the β-1,3-glucan is schizophyllan.

12. The nucleic acid polymer complex of claim 10, wherein the nucleic acid comprises RNA or DNA.

13. The nucleic acid polymer complex of claim 10, wherein the β-1,3-glucan is curdlan, lentinan, pachyman, griffollan or scleroglucan.

14. The nucleic acid polymer complex of claim 10, wherein the hydrogen-bonding polymer has a weight-average molecular weight of 2000 or more.

15. The nucleic acid polymer complex of claim 10, wherein the hydrogen-bonding polymer has an h/R value in a range of 2 to 4 Å.

16. An aqueous solution comprising the nucleic acid-polymer complex of claim 10.

17. An isolated nucleic acid-polymer complex composed of a nucleic acid and a hydrogen bonding polymer having a polymer chain, the hydrogen bonding polymer consisting of β-1,3-glucan, the complex being formed by a method comprising:
   unbinding a triple helix structure comprising a naturally occurring β-1,3-glucan to form a single strand comprising a hydrogen bonding polymer having a polymer chain with hydrogen-bonding sites on the polymer chain; and
   combining the hydrogen bonding polymer with an aqueous solution of a single stranded nucleic acid to form the complex through the hydrogen-bonding sites on the polymer chain, the single stranded nucleic acid comprising poly(A), poly (C) or poly(dA), the poly(A), poly (C) or poly(dA) of the nucleic acid being a helical compound which has helix parameters similar to that of the hydrogen bonding polymer.

18. The nucleic acid polymer complex of claim 17, wherein the polymer chain has an h/R value in a range of 2 to 4 Å.

19. The isolated nucleic acid-polymer complex of claim 17, wherein the unbinding of the triple helix structure includes dissolving the β-1,3-glucan in a solvent.

20. The isolated nucleic acid-polymer complex of claim 19, wherein the solvent comprises DMSO.

21. The isolated nucleic acid-polymer complex of claim 17, wherein the nucleic acid is an antisense DNA linked to a poly(dA).

22. The isolated nucleic acid-polymer complex of claim 17, wherein said polymer chain has helix parameters sufficiently similar to the helix parameters of the nucleic acid for a complex to be formed between said nucleic acid and said hydrogen bonding polymer.

23. The nucleic acid polymer complex of claim 17, wherein the naturally occurring β-1,3-glucan is schizophyllan.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Escherichia coli

<400> SEQUENCE: 1
ctttaagaag gagatatacc                    20

<210> SEQ ID NO 2
<211> LENGTH: 20
<212> TYPE: DNA
<213> ORGANISM: Artificial
<220> FEATURE:
<223> OTHER INFORMATION: Antisense DNA

<400> SEQUENCE: 2
ggtatatctc cttcttaaag                    20